(12) United States Patent
Scates et al.

(10) Patent No.: US 8,975,452 B2
(45) Date of Patent: Mar. 10, 2015

(54) PROCESS FOR PRODUCING ETHANOL BY HYDROCARBON OXIDATION AND HYDROGENATION OR HYDRATION

(75) Inventors: Mark Scates, Houston, TX (US); Heiko Weiner, Pasadena, TX (US); Zhenhua Zhou, Houston, TX (US); James Zink, League City, TX (US)

(73) Assignee: Celanese International Corporation, Dallas, TX (US)

( * ) Notice: Subject to any disclaimer, the term of this patent is extended or adjusted under 35 U.S.C. 154(b) by 303 days.

(21) Appl. No.: 13/432,849

(22) Filed: Mar. 28, 2012

(65) Prior Publication Data

US 2013/0261347 A1 Oct. 3, 2013

(51) Int. Cl.
| | |
|---|---|
| C07C 29/149 | (2006.01) |
| C07C 1/22 | (2006.01) |
| C07C 5/48 | (2006.01) |
| C07C 9/06 | (2006.01) |
| C07C 11/04 | (2006.01) |
| C07C 29/04 | (2006.01) |
| C07C 29/16 | (2006.01) |
| C07C 29/74 | (2006.01) |
| C07C 31/08 | (2006.01) |
| C07C 51/215 | (2006.01) |
| C07C 53/08 | (2006.01) |

(52) U.S. Cl.
CPC ............... *C07C 29/149* (2013.01); *C07C 1/22* (2013.01); *C07C 5/48* (2013.01); *C07C 9/06* (2013.01); *C07C 11/04* (2013.01); *C07C 29/04* (2013.01); *C07C 29/16* (2013.01); *C07C 29/74* (2013.01); *C07C 31/08* (2013.01); *C07C 51/215* (2013.01); *C07C 53/08* (2013.01)
USPC ........................................................ 568/885

(58) Field of Classification Search
CPC ....... C07C 29/149; C07C 53/08; C07C 29/74; C07C 29/76; C07C 29/80
USPC ........................................................ 568/885
See application file for complete search history.

(56) References Cited

U.S. PATENT DOCUMENTS

| | | | |
|---|---|---|---|
| 3,478,112 A | 11/1969 | Karl et al. |
| 3,769,329 A | 10/1973 | Paulik et al. |
| 3,772,380 A | 11/1973 | Paulik et al. |
| 3,864,284 A | 2/1975 | Clippinger et al. |
| 4,317,918 A | 3/1982 | Takano et al. |
| 4,352,947 A | 10/1982 | Habib et al. |
| 4,421,939 A | 12/1983 | Kiff et al. |
| 4,476,326 A | 10/1984 | Lin et al. |
| 4,497,967 A | 2/1985 | Wan |
| 4,517,391 A | 5/1985 | Schuster et al. |
| 4,692,218 A | 9/1987 | Houben et al. |
| 4,758,600 A | 7/1988 | Arimitsu et al. |
| 4,777,303 A | 10/1988 | Kitson et al. |
| 4,804,791 A | 2/1989 | Kitson et al. |
| 4,826,795 A | 5/1989 | Kitson et al. |
| 4,990,655 A | 2/1991 | Kitson et al. |
| 5,008,235 A | 4/1991 | Wegman et al. |
| 5,017,731 A | 5/1991 | Gesser et al. |
| 5,061,671 A | 10/1991 | Kitson et al. |
| 5,137,861 A | 8/1992 | Shih et al. |
| 5,149,680 A | 9/1992 | Kitson et al. |
| 5,162,578 A | 11/1992 | McCain, Jr. et al. |
| 5,185,476 A | 2/1993 | Gustafson |
| 5,243,095 A | 9/1993 | Roberts et al. |
| 5,599,976 A | 2/1997 | Scates et al. |
| 5,821,111 A | 10/1998 | Gaddy et al. |
| 5,955,397 A | 9/1999 | Didillon et al. |
| 6,232,352 B1 | 5/2001 | Vidalin et al. |
| 6,458,996 B1 | 10/2002 | Muskett |
| 6,462,231 B1 | 10/2002 | Yanagawa et al. |
| 6,472,555 B2 | 10/2002 | Choudary et al. |
| 6,486,366 B1 | 11/2002 | Ostgard et al. |
| 6,495,730 B1 | 12/2002 | Konishi et al. |
| 6,509,180 B1 | 1/2003 | Verser et al. |
| 6,559,333 B1 | 5/2003 | Brunelle et al. |
| 6,632,330 B1 | 10/2003 | Colley et al. |
| 6,867,164 B2 | 3/2005 | Obana et al. |
| 6,906,228 B2 | 6/2005 | Fischer et al. |
| 6,927,048 B2 | 8/2005 | Verser et al. |
| 7,084,312 B1 | 8/2006 | Huber et al. |
| 7,208,624 B2 | 4/2007 | Scates et al. |
| 7,297,236 B1 | 11/2007 | Vander Griend et al. |
| 7,375,049 B2 | 5/2008 | Hayes et al. |
| 7,507,562 B2 | 3/2009 | Verser et al. |
| 7,538,060 B2 | 5/2009 | Barnicki et al. |
| 7,553,397 B1 | 6/2009 | Colley et al. |
| 7,572,353 B1 | 8/2009 | Vander et al. |
| 7,608,744 B1 | 10/2009 | Johnston et al. |
| 7,700,814 B2 | 4/2010 | Garton et al. |
| 7,842,844 B2 | 11/2010 | Atkins |
| 7,863,489 B2 | 1/2011 | Johnston et al. |
| 7,947,746 B2 | 5/2011 | Daniel et al. |
| 8,071,389 B2 | 12/2011 | Weck et al. |
| 8,071,821 B2 | 12/2011 | Johnston et al. |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

(Continued)

*Primary Examiner* — Elvis O Price

(57) ABSTRACT

Hydrocarbons are oxidized to ethylene and/or oxygenates that comprise acetic acid. The acetic acid may be converted to ethanol by hydrogenation. The ethylene may be converted to ethanol by hydration.

18 Claims, 3 Drawing Sheets

(56) References Cited

U.S. PATENT DOCUMENTS

| | | |
|---|---|---|
| 2003/0077771 A1 | 4/2003 | Verser et al. |
| 2003/0104587 A1 | 6/2003 | Verser et al. |
| 2003/0114719 A1 | 6/2003 | Fischer et al. |
| 2006/0019360 A1 | 1/2006 | Verser et al. |
| 2006/0127999 A1 | 6/2006 | Verser et al. |
| 2008/0207953 A1 | 8/2008 | Houssin et al. |
| 2009/0023192 A1 | 1/2009 | Verser et al. |
| 2009/0069609 A1 | 3/2009 | Kharas et al. |
| 2010/0029995 A1 | 2/2010 | Johnston et al. |
| 2010/0029996 A1 | 2/2010 | Danjo et al. |
| 2010/0063319 A1 | 3/2010 | Brtko et al. |
| 2010/0121114 A1 | 5/2010 | Johnston et al. |
| 2010/0145097 A1 | 6/2010 | Brtko et al. |
| 2010/0197485 A1 | 8/2010 | Johnston et al. |
| 2010/0197985 A1 | 8/2010 | Johnston et al. |
| 2010/0273229 A1 | 10/2010 | Verser et al. |
| 2011/0004033 A1 | 1/2011 | Johnston et al. |
| 2011/0004034 A1 | 1/2011 | Daniel et al. |
| 2011/0046421 A1 | 2/2011 | Daniel et al. |
| 2011/0082322 A1 | 4/2011 | Jevtic et al. |
| 2011/0098501 A1 | 4/2011 | Johnston et al. |
| 2011/0185630 A1 | 8/2011 | Horton et al. |
| 2011/0190547 A1 | 8/2011 | Jevtic et al. |
| 2011/0190548 A1 | 8/2011 | Jevtic et al. |
| 2011/0224462 A1 | 9/2011 | Ditzel et al. |
| 2011/0275862 A1 | 11/2011 | Johnston et al. |
| 2011/0275864 A1 | 11/2011 | Warner et al. |
| 2011/0275865 A1 | 11/2011 | Warner et al. |

FOREIGN PATENT DOCUMENTS

| | | |
|---|---|---|
| CN | 102229520 | 11/2011 |
| EP | 0137749 | 4/1985 |
| EP | 0167300 | 1/1986 |
| EP | 0175558 | 3/1986 |
| EP | 0192587 | 8/1986 |
| EP | 0198682 | 10/1986 |
| EP | 0990638 | 4/2000 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 2001-046874 | 2/2001 |
| JP | 2001-157841 | 6/2001 |
| WO | WO 82/03854 | 11/1982 |
| WO | WO 83/03409 | 10/1983 |
| WO | WO 03/106396 | 12/2003 |
| WO | WO 2004/026805 | 4/2004 |
| WO | WO 2007/003897 | 1/2007 |
| WO | WO 2009/009320 | 1/2009 |
| WO | WO 2009/063174 | 5/2009 |
| WO | WO 2009/063176 | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2009/103948 | 8/2009 |
| WO | WO 2010/014151 | 2/2010 |
| WO | WO 2010/014153 | 2/2010 |
| WO | WO 2010/030320 | 3/2010 |
| WO | WO 2010/055285 | 5/2010 |
| WO | WO 2011/053365 | 5/2011 |

OTHER PUBLICATIONS

Yang et al., Process of Ethanol Synthesis through esterification of acetic acid and economic analysis. No. 4, 2011, 15 Pages.

T. Yokoyama, et al., "Carboxylic Acids and Derivatives", Fine Chemicals through Heterogenous Catalysis, pp. 370-379.

Rachmady, Acetic Acid Reduction by H2 on Bimetallic Pt—Fe Catalysts, Journal of Catalysis 209, 87-98 (Apr. 1, 2002), Elsevier Science (USA).

Alcala, et al., (2005). Experimental and DFT studies of the conversion of ethanol and acetic acid on PtSn-based catalysts, Journal of Physical Chemistry, 109(6), 2074-2085.

PROCESS FOR PRODUCING ETHANOL BY HYDROCARBON OXIDATION AND HYDROGENATION OR HYDRATION

FIELD OF THE INVENTION

The present invention relates generally to processes for producing ethanol and, in particular, to a process for making ethanol from hydrocarbons, such as ethane, and oxygenates, such as acetic acid. The oxygenates may be produced by the oxidation of hydrocarbons.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

U.S. Pat. No. 5,017,731 describes a process for directly converting ethane to ethanol and methanol using controlled oxidation. The reaction takes place in an inert reactor, i.e., one having internal surfaces which do not affect the reaction, in the absence of a catalyst. The ethane is intimately mixed with air or oxygen prior to the introduction of the mixed gases into a heated pre-reactor which allows the pre-reaction or induction period to proceed. The pre-reacted gases then enter the reactor where the reaction takes place at elevated temperatures of 200° C. to 350° C. and at elevated pressure from 10 to 150 atmospheres. The percentage of oxygen in the mixture of reactant gases is kept below 15% by volume and is preferably 2 to 10% by volume.

U.S. Pat. No. 5,162,578 describes a process for producing acetic acid by a catalytic oxidation with oxygen of ethane, or ethylene, or mixtures thereof. Two different catalysts are used for the oxidative dehydrogenation of ethane and subsequent hydration of ethylene or oxidation of ethylene oxidation to acetic acid.

The need remains for processes for making ethanol from available industrial sources.

SUMMARY OF THE INVENTION

In a first embodiment, the present invention is directed to a process for producing ethanol, the process comprising the steps of: (a) contacting ethane with oxygen under conditions effective to form oxygenates; and (b) passing hydrogen and at least a portion of the oxygenates from step (a) to a hydrogenation reactor, wherein at least a portion of the oxygenates are reacted with hydrogen to produce ethanol. In one preferred embodiment, substantially no methanol is produced in step (a) or step (b). The oxygenates may comprise acetaldehyde and/or at least 80 wt. % acetic acid. At least 10% of ethane is converted to oxygenates in step (a) with a selectivity to acetic acid of at least 50%. The feed to the hydrogenation reactor of step (b) comprises acetic acid produced in step (a) and acetic acid from a source other than ethane oxidation, wherein the source is carbonylation or fermentation. Additionally, from 1 to 60% of the acetic acid introduced into hydrogenation reaction zone is obtained from step (a) and from 40 to 99% of the acetic acid introduced into hydrogenation reaction zone is obtained from the source other than ethane oxidation. Step (a) may be conducted in the presence of a catalyst comprising Mo, Pd, Re and at least one other metal. Step (b) may also be conducted in the presence of a catalyst, the catalyst comprising a first metal, oxides thereof, or carbides thereof selected from the group consisting of cobalt, rhodium, rhenium, ruthenium, platinum, palladium, osmium, iridium, molybdenum, and gold, a second metal or oxides thereof selected from the group consisting of copper, iron, tin, cobalt, nickel, zinc, and molybdenum, and an optional third metal or oxides thereof selected from the group consisting of copper, molybdenum, tin, chromium, iron, cobalt, vanadium, palladium, platinum, lanthanum, cerium, manganese, ruthenium, rhenium, gold, and nickel, wherein the second metal is different than the first metal and the optional third metal.

In a second embodiment, the present invention is directed to a process for producing ethanol, the process comprising the steps of: (a) contacting ethane with oxygen under conditions effective to form oxygenates and ethylene; and (b) passing hydrogen, at least a portion of the oxygenates from step (a) and at least a portion of the ethylene from step (a) to a hydrogenation reactor, wherein at least a portion of the oxygenates are reacted with hydrogen to produce ethanol. Step (a), conducted in the presence of a catalyst comprising molybdenum, vanadium, oxides thereof, carbides thereof or combinations thereof, produces from 30 to 90 wt. % oxygenates and 10 to 70 wt. % ethylene, wherein the oxygenates comprise acetaldehyde and/or acetic acid. At least a portion of the ethylene in the hydrogenation reactor of step (b) is hydrated to form ethanol. Additionally, at least a portion of the ethylene in the hydrogenation reactor of step (b) is hydrogenated to form ethane, which is recycled to step (a). Step (b) is conducted in the presence of a catalyst comprising a first metal, oxides thereof or carbides thereof selected from the group consisting of cobalt, rhodium, rhenium, ruthenium, platinum, palladium, osmium, iridium and gold, a second metal or oxides thereof selected from the group consisting of copper, iron, tin, cobalt, nickel, zinc, and molybdenum, and an optional third metal or oxides thereof selected from the group consisting of copper, molybdenum, tin, chromium, iron, cobalt, vanadium, palladium, platinum, lanthanum, cerium, manganese, ruthenium, rhenium, gold, and nickel, wherein the second metal is different than the first metal and the optional third metal. At least a portion of the acetic acid in step (a) is derived from carbonylation or fermentation. In one preferred embodiment, substantially no methanol is produced in step (a) or step (b).

In a third embodiment, the present invention is directed to a process for producing ethanol, the process comprising the steps of: (a) contacting ethane with oxygen under conditions effective to form ethylene; and (b) contacting the thus produced ethylene with water under hydration conditions effective to form ethanol. The conversion of ethane in step (a) is at least 10% with a selectivity to ethylene of at least 50%. Step (a) is conducted in the presence of a first catalyst comprising Mo, V, Nb, Sb, oxides thereof, carbides thereof, or combinations thereof. Step (b) is conducted in the presence of a second catalyst that is selected from the group consisting of phosphoric acid, sulfuric acid, tungstic acid, heteropoly acid salt and anion ion exchange resin. In one preferred embodiment, substantially no methanol is produced in step (a) or step (b).

In a fourth embodiment, the present invention is directed to a process for producing ethanol, the process comprising the steps of: (a) contacting acetic acid and hydrogen in a first reactor under conditions effective to form ethanol and ethane; (b) separating the ethanol and ethane to form an ethanol stream and an ethane stream; and (c) passing at least a portion of the ethane and oxygen to a second reactor to form a second reactor product comprising oxygenates; and (d) introducing at least a portion of the second reactor product into the first reactor. In one preferred embodiment, substantially no methanol is produced in step (a), step (b), step (c) or step (d). The second reactor also forms ethylene, which is introduced to the first reactor with at least a portion of the oxygenates. In some embodiments, the second reactor product comprises more acetic acid than ethylene, on a weight basis. The oxygenates may comprise acetaldehyde and/or acetic acid. In some embodiments, the oxygenates may comprise at least 80 wt. % acetic acid. When the second reactor product comprises more than 50 wt. % ethylene, step (c) may further comprise (i) separating the second reactor product to form an oxygenates stream and an ethylene stream; and (ii) feeding the oxygenates stream to the first reactor. The ethanol and ethane may be separated using liquid-vapor separation. The ethanol stream may be substantially free of ethane and the ethane stream may be substantially free of ethanol. The ethane stream may comprise at least 90 vol. % ethane. In additional embodiments, the process may further comprise (e) contacting the ethylene stream with water in a third reactor to form ethanol; (f) separating the ethanol and unreacted ethylene; and (g) combining the unreacted ethylene with the ethane from step (c).

In a fifth embodiment, the present invention is directed to a process for producing ethanol, the process comprising the steps of: (a) providing a crude stream comprising ethanol and ethane; (b) separating the ethanol and ethane to form an ethanol stream and an ethane stream; (c) passing at least a portion of the ethane and oxygen to a second reactor to form a second reactor product comprising oxygenates; and (d) introducing at least a portion of the second reactor product into the first reactor. The second reactor product may further comprise ethylene.

In a sixth embodiment, the present invention is directed to a process for producing ethanol, the process comprising the steps of: (a) contacting a feed stream comprising ethylene and at least one of acetic acid or ethyl acetate with hydrogen in a first reactor, under conditions effective to form a first reactor product comprising ethanol and ethane; (b) separating the ethanol and ethane to form an ethanol stream and an ethane stream; (c) passing at least a portion of the ethane stream and oxygen to a second reactor to form a second reactor product comprising oxygenates, ethylene, or mixtures thereof; and (d) introducing at least a portion of the second reactor product into the first reactor. The first reactor may comprise a polymerization inhibitor. The feedstream may comprise ethyl acetate and 0.5 to 10 mol. % ethylene.

In a seventh embodiment, the present invention is directed to a process for producing ethanol, the process comprising the steps of: (a) contacting a $C_n$ alkane with oxygen under conditions effective to form $C_n$ oxygenates and/or a $C_n$ alkene; and (b) passing hydrogen, at least a portion of the $C_n$ oxygenates from step (a) and/or at least a portion of the $C_n$ alkene from step (a) to a hydrogenation reactor, wherein at least a portion of the $C_n$ oxygenates are reacted with hydrogen to produce a $C_n$ alcohol, wherein n is from 2 to 5. In one preferred embodiment, substantially no methanol is produced in step (a) or step (b). The $C_n$ oxygenates comprise a $C_n$ aldehyde and a $C_n$ carboxylic acid. At least a portion of the $C_n$ alkene in the hydrogenation reactor of step (b) is hydrogenated to form a $C_n$ alkane, and wherein the $C_n$ alkane is recycled from step (b) to step (a). The feed to the hydrogenation reactor of step (b) comprises $C_n$ carboxylic acid produced in step (a), $C_n$ carboxylic acid from a separate source, an anhydride of $C_n$ carboxylic acid and a $C_m$ alkyl ester of a $C_n$ carboxylic acid, where m is from 2 to 5, and where m and n are the same or different.

In an eighth embodiment, the present invention is directed to a process for producing ethanol, the process comprising (a) passing hydrogen and acetic acid, wherein the acetic acid is derived from at least two different sources, to a reactor, and (b) reacting the hydrogen and acetic acid in the presence of a catalyst to produce ethanol, wherein at least one of the different sources of acetic acid is ethane oxidation. Ethane oxidation may be conducted in the presence of a catalyst comprising Mo, Pd, Re and at least one other metal. Preferably, there is no substantially no methanol. The different source further comprises acetaldehyde, ethylene and acetic anhydride. The different source may additionally comprise methyl acetate or ethyl acetate. The different source of acetic acid is produced by reacting methanol with carbon monoxide in a carbonylation reaction.

DETAILED DESCRIPTION OF THE INVENTION

A. Introduction

In general, the process relates to producing ethanol from hydrocarbons, including ethane. In one embodiment, ethane may be oxidized to produce oxygenates that are further hydrogenated to ethanol. In another embodiment, ethane may be oxidized to produce oxygenates and ethylene that are further reacted, via hydrogenation or hydration, to ethanol. In still another embodiment, ethane may be oxidized to produce ethylene that is further hydrated to ethanol or converted to ethane that can be recycled to the oxidization reactor.

The oxygenates may comprise acetic acid, acetaldehyde, ethyl acetate, ethanol, and mixtures thereof. More preferably, the oxygenates may comprise at least acetic acid. The oxidation catalyst may produce a mixture of oxygenates or one species of the oxygenates, such as acetic acid.

In some embodiments, the oxidation catalysts may be more selective for producing ethylene or one of the oxygenate species, such as acetic acid or acetaldehyde. When selective for one species, the oxidation reaction product, also referred to as the second reactor product, may comprise at least 80 wt. % of that species, e.g., at least 90 wt. % of that species. When acetic acid is the primary species in the second reactor product, it is preferred that the oxygenates comprise at least 80 wt. % acetic acid, and that the second reactor product may also contains low amounts of ethylene, e.g. from 0.1 to 5 wt. % ethylene. When ethylene is the primary species, it is preferred that the second reactor product comprises at least 80 wt. % ethylene, and contains low amounts of acetic acid, e.g. from 0.1 to 5 wt. % acetic acid.

In other embodiments, the catalyst for oxidizing ethane may produce a mixture of products. In one exemplary embodiment, the oxygenates may comprise a mixture comprising from 25 to 80 wt. % acetic acid, from 0.1 to 40 wt. % acetaldehyde, 0.1 to 40 wt. % ethanol, and from 0.01 to 10 wt. % ethyl acetate. More preferably, the oxygenates may comprise a mixture comprising from 40 to 80 wt. % acetic acid, from 5 to 25 wt. % acetaldehyde, 0.1 to 15 wt. % ethanol, and from 0.01 to 1 wt. % ethyl acetate.

In addition, the ethane may also produce a mixture comprising ethylene. Based on the total oxidation reactor products, the oxygenates be present from 30 to 90 wt. % and ethylene from 10 to 70 wt. %. More preferably, the oxygenates may be present in total oxidation reactor products from 40 to 75 wt. % and ethylene from 25 to 60 wt. %.

Figure 1:
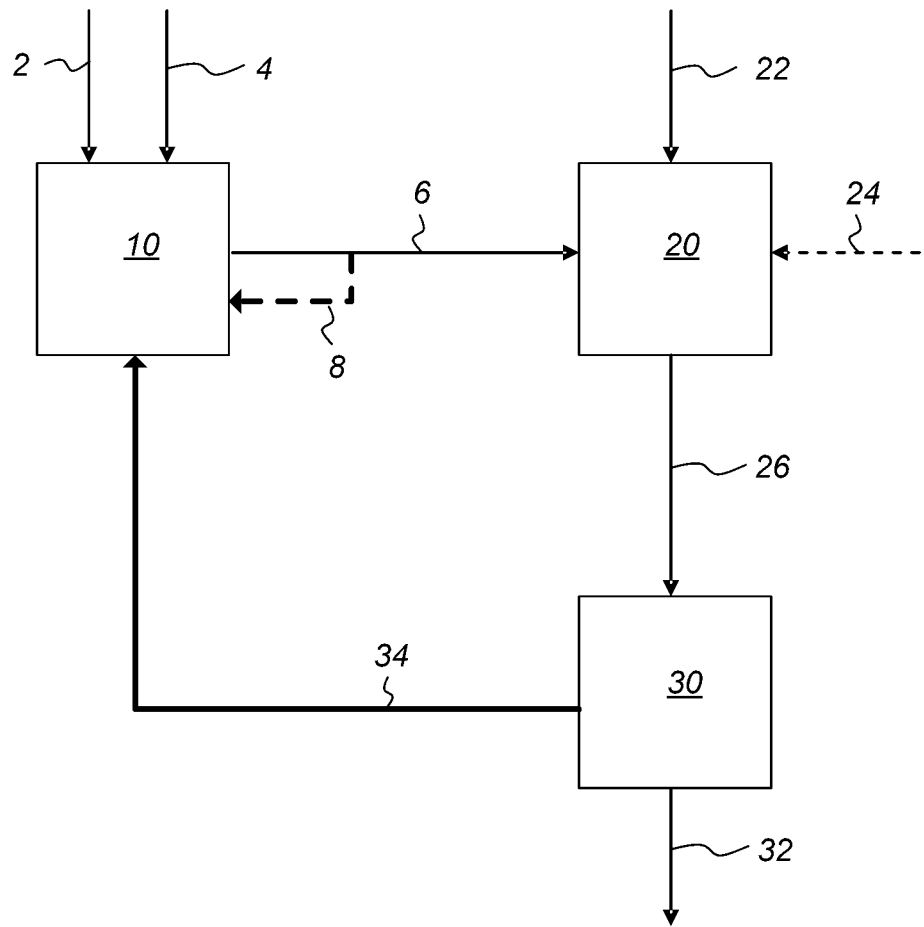
FIG. 1 is a representation of an integrated process for oxidizing ethane to produce oxygenates and hydrogenating oxygenates to produce ethanol in accordance with an embodiment of the present invention.

FIG. 1 provides a flow diagram of an example of an integrated process for producing acetic acid by oxidation of ethane and hydrogenation of acetic acid produced by ethane oxidation. It will be understood that lines depicted in FIG. 1, such as lines 2, 6 and 22, depict flow of materials through the process, rather than specific apparatus or equipment, such as pipes.

In FIG. 1, a feed comprising ethane is introduced through line 2 into an oxidation reaction zone 10. The ethane feed may also comprise other compounds, such as ethylene and/or methane. Another feed comprising oxygen, e.g., pure oxygen or air, is also introduced into the oxidation reaction zone 10 through line 4. Optionally, the ethane and oxygen may be premixed before being introduced into the oxidation reaction zone 10 through a single line. The percent of oxygen in the reactant gases may be less than 15% by volume, e.g., less than 10% by volume. A suitable oxidation catalyst, as discussed herein, may also be introduced into the oxidation reaction zone 10. Preferably, the catalyst may be selective for producing acetic acid or a mixture of acetic acid and ethylene.

Line 6 represents the transfer of the oxidation products to hydrogenation zone 20. The oxidation products may comprise oxygenates and/or ethylene. A hydrogen feed is introduced into hydrogenation zone 20 via line 22. An optional feed of additional acetic acid, e.g., from a source other than ethane oxidation, may be introduced into hydrogenation zone 20 via line 24. Optionally, the hydrogen feed and/or the additional acetic acid feed may be combined with the ethane oxidation product feed before being introduced into the hydrogenation zone 20.

Although the oxidation reaction product may comprise a sufficient amount of acetic acid to produce ethanol, in some optional embodiments, an optional feed of additional acetic acid in line 24 may be used when the content of the oxidation product in line 6 is low. An optional feed of additional acetic acid may not be excluded in some embodiments. The source of additional acetic acid may come from, for example, carbonylation or fermentation of a suitable biological material. In one embodiment, the volumetric ratio of oxidation product to the optional additional acetic acid may be from 10:1 to 1:10, e.g., from 5:1 to 1:5 or from 3:1 to 1:3. In terms of mass percentages, in one embodiment, from 1 to 60% of the acetic acid, and more preferably from 5 to 50%, introduced into hydrogenation reaction zone 20 may be generated in oxidation reaction zone 10 and fed via line 6. Also, from 40 to 99% of the acetic acid, and more preferably from 50 to 95%, introduced into hydrogenation reaction zone 20 may be generated from a source other than from the effluent from the oxidation reaction zone 10 and introduced via optional line 24.

In FIG. 1, the entire oxidation reaction product in line 6 from the oxidation reaction zone 10, including oxygenates and ethylene if any, is introduced into the hydrogenation reaction zone 20. In other words, there is no separation of the oxygenates and ethylene, if any. In another embodiment, the crude product from the oxidation reaction zone 10 is at least partially refined before being introduced into the hydrogenation zone 20. For example, at least a portion of any unreacted ethane exiting the oxidation zone may be diverted from line 6, e.g., and recycled to the oxidation reaction zone 10 via optional line 8. In addition, optional line 8 may also comprise a portion of ethylene, if produced in oxidation reaction zone.

Product from the hydrogenation zone 20 is transferred to separation zone 30 via line 26. At least two streams may be recovered from the separation zone 30. One of these streams may comprise a refined ethanol product, which is represented in FIG. 1 as being withdrawn from separation zone 30 via line 32. Another stream, which may be recovered from separation zone 30, may comprise ethylene and/or ethane. Such ethylene and/or ethane may be recycled to the oxidation reaction zone 10. The transfer of ethylene and/or ethane recovered from the separation zone 30 to oxidation reaction zone 10 may take place via line 34.

Figure 2:
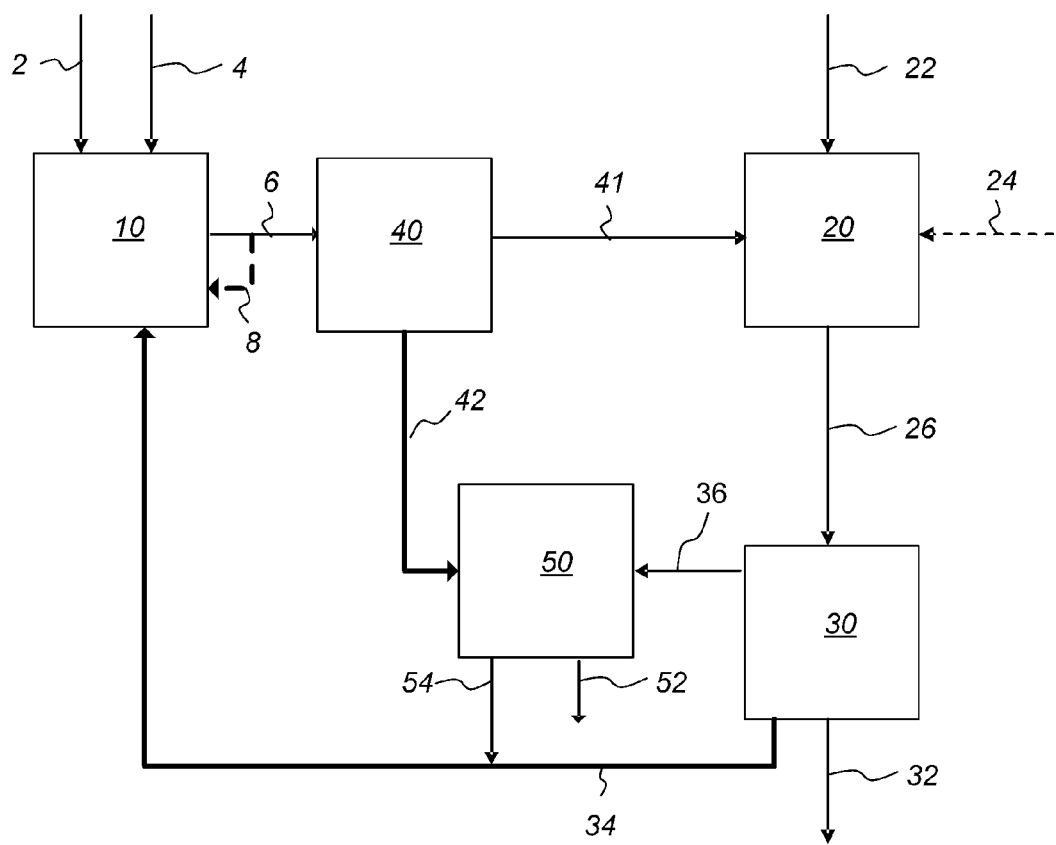
FIG. 2 is a representation of an integrated process for oxidizing ethane to produce oxygenates, and separate reactors for hydrogenating oxygenates and hydrating ethylene in accordance with an embodiment of the present invention.

In FIG. 2, the oxidation reaction product in line 6 is separated in zone 40 into an oxygenate stream 41 and an ethylene stream 42. Oxygenate stream 41 is fed to hydrogenation reactor 20. Oxygenate stream 41 may comprise more acetic acid than ethylene, on a weight percent basis. Ethylene stream 42 is fed to a hydration zone 50 along with water in line 36. In one embodiment, the hydration zone 50 may comprise a catalyst selected from the group consisting of phosphoric acid, sulfuric acid, tungstic acid, heteropoly acid salt and anion ion exchange resin. In one embodiment, the water may be obtained from separation zone 30. Hydration reactor produces an ethanol product in line 52, which may be combined with refined ethanol product in line 32. Unreacted ethylene may be separated and returned to oxidation reaction zone 10 via line 54.

Figure 3:
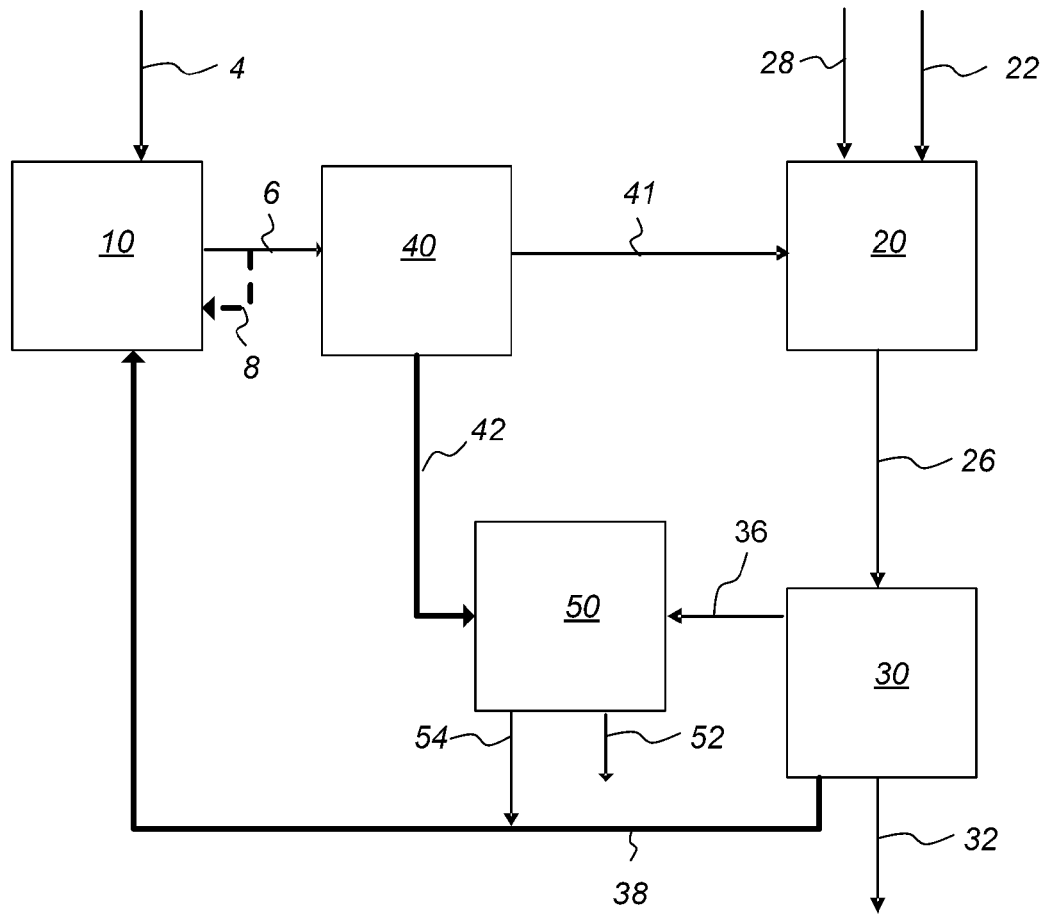
FIG. 3 is a representation of process for oxidizing by-product ethane from a hydrogenation reaction in accordance with an embodiment of the present invention.

In another embodiment, the ethane may be a by-product from the hydrogenation reaction as shown in FIG. 3. Acetic acid in line 28 and hydrogen in line 22 are fed to hydrogenation reactor 20.

In some embodiments, the feed stream to hydrogenation reactor 20 comprises ethylene and at least one of acetic acid or ethyl acetate, wherein hydrogenation reactor 20 may comprise a polymerization inhibitor. Suitable polymerization inhibitors include but are not limited to hydroquinone, benzoquinone, tertiary-butyl catechol, alphamethylstyrene, nitric oxide, and phenols. The phenols include alkyl phenols, such as nitrobenzene and 1,3,5-trinitrobenzene, that are disclosed in U.S. Pat. No. 4,021,476, the entirety of which is hereby incorporated by reference. In some embodiments, the feedstream comprises ethylene and ethyl acetate. In further embodiments, the feedstream comprises from 0.5 to 10 mol. % ethylene, e.g., from 0.5 to 7.5 mol. % ethylene or from 0.5 to 5 mol. % ethylene.

The crude ethanol product in line 26 may comprise ethanol, and ethane. Ethane may be present from 0.5 to 10 mol %. Ethanol and ethane may then be separated. In some embodiments, they are separated using liquid-vapor separation. Normally, ethane is purged from the hydrogenation in separation zone 30. However, in one embodiment, ethane is concentrated in line 38 and is directed to an oxidation reaction zone 10 and reacted with oxygen in line 4 to produce oxidation reaction product in line 6. By concentrating ethane, the process may obtain at least 95% of the ethane from the hydrogenation reactor in the concentrated stream in line 38. Oxidation reaction product in line 6 may be directly fed to hydrogenation reactor 20 as described above in FIG. 1, or directed to zone 40 as shown to yield an oxygenate stream 41 and an ethylene stream 42 as described above in FIG. 2. This may allow for recapture of the ethane to increase ethanol productivity.

The second reactor product, oxidation reaction product in line 6, may comprise ethylene. When the second reactor product comprises more than 50 wt. % ethylene, e.g., more than 55 wt. % ethylene or more than 60 wt. % ethylene, the second reactor product is separated to form an oxygenates stream and an ethylene stream. The oxygenates stream is then fed to the first reactor, hydrogenation reactor 20. The ethylene stream may be contacted with water in a third reactor in hydration zone 50 to form ethanol. The ethanol may be separated from any unreacted ethylene and the unreacted ethylene may then be combined with the ethane in line 38.

The oxygenates in the second reactor product comprise acetaldehyde and/or acetic acid. In some embodiments, the oxygenates comprise at least 80 wt. % acetic acid. In other embodiments, the second reactor product comprises more acetic acid than ethylene, on a weight basis.

When ethane is separated in separation zone 30 from crude ethanol product in line 26, refined ethanol product in line 32 may be substantially free of ethane. Line 38 may be substantially free of ethanol. Line 38 comprises at least 90 vol. % ethane, e.g., at least 95 vol. % ethane or at least 99 vol. % ethane. Line 38 may further comprise other gases, including hydrogen, carbon dioxide, and carbon monoxide, which may be separated from ethane (not shown) prior to recycling ethane to oxidation reaction zone 10.

B. Oxidation of Hydrocarbons

Catalysts for oxidizing hydrocarbons, including ethane, may include those that are capable of producing mixed products, including mixed oxygenates, and catalysts that are selective for one species, such as acetic acid or ethylene, may be used in embodiments of the present invention. Generally, the oxygenates should at least comprise either acetic acid or acetaldehyde. Catalysts capable of converting ethane to either of these species are preferably used.

Catalysts for oxidizing ethane to oxygenates, and in particular acetic acid, and catalysts for oxydehydrogenation reactions, i.e. which primarily produce ethylene from ethane, include catalysts containing molybdenum and/or vanadium, including oxides thereof. Suitable catalysts are described in U.S. Pat. Nos. 4,250,346; 4,524,236; 4,568,790; 6,034,270; 6,274,765; 6,399,816; 6,906,221; 7,015,355; and 7,081,549, each of which is incorporated herein by reference in its entirety. Exemplary catalysts may comprise molybdenum and at least one metal selected from the group consisting of niobium, vanadium, titanium, tungsten, tantalum, palladium, rhenium, lead, antimony, iron, bismuth, and silicon. In particular, the catalyst that may be selective to ethylene and may be an oxide or carbide catalyst comprising Mo, V, Nb, Sb, or combinations thereof. An additional metal may also be present in the oxide or carbide catalyst. Another oxide or carbide catalyst may be more selective to acetic acid and may comprise Mo, Pd, Re, and at least one other metal. The oxide or carbide catalysts may be on a support that is selected from the group consisting of silica, alumina, silica-alumina, silicon carbide, titania, zirconia, and mixtures thereof. Other inorganic oxides or carbides may also be used. Preferred support materials have a surface area of less than 100 $m^2$/g. The metals or oxides thereof may be impregnated on the support using incipient wetness techniques.

The hydrocarbon oxidation and/or oxidative dehydrogenation reaction is preferably carried out in the presence of added water (steam) in the gas phase at a temperature less than 550° C., e.g., from 200° C. to 400° C. The reaction pressure may be from 1 to 50 atm, and more preferably from 1 to 20 atm. In one embodiment, one mole of ethane may be reacted with 0.01 to 0.5 moles of molecular oxygen, either in the form of pure oxygen or air. Higher oxygen contents are preferred, since the achievable ethane conversion and thus the yield of oxygenates may be higher. It is preferred to add oxygen or gas containing molecular oxygen in a concentration range outside the explosion limits under reaction conditions, since this simplifies performance of the process. However, it is also possible to set the ethane to oxygen molar ratio within the explosion limits. The hydrocarbon oxidation reaction may be carried out in a fluidized bed or a fixed-bed reactor.

In one embodiment, the conversion of ethane may be at least 10%, e.g., at least 30% or at least 50%. The selectivity to ethylene, for oxidative dehydrogenation reactions, is preferably at least 50%, e.g., at least 60% or at least 75%. The selectivity to acetic acid, for hydrocarbon oxidation reactions, is preferably at least 50%, e.g., at least 60% or at least 75%. More preferably, the hydrocarbon oxidation reactions produce low amounts of hydrogen and methane, which reduces the necessity to separate the hydrocarbon oxidation reaction product. Although, the catalyst may favor one species over the other, some of the catalyst may also produce a mixture of ethylene and acetic acid as described in U.S. Pat. No. 4,250,346, which is incorporated herein by reference in its entirety.

Ethane may be obtained from a raw material such as natural gas or a by-product of petroleum refining. In addition, in some embodiments, ethane may be a by-product of hydrogenating acetic acid to ethanol. Preferably, ethane is a gaseous stream comprising at least 3 vol. % of ethane, at atmospheric pressure. The ethane stream may comprise $N_2$, $CO_2$, $CH_4$, and/or $H_2O$. There may be other minor components such as $H_2$, CO, higher alkanes and alkenes. In one embodiment, the catalysts for converting ethane to ethylene are not selective for converting higher alkanes, but rather burn these materials to CO and other oxidized carbonaceous products.

C. Other Acetic Acid Sources

As stated above, in some optional embodiments, in addition to the acetic acid in the oxygenates produced by hydrocarbon oxidation, there may be a source optional source of acetic acid that may be added to the reactor. For example, the optional source of acetic acid may be produced by methanol carbonylation, methyl acetate carbonylation, dimethyl ether carbonylation, acetaldehyde oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described hydrogenation process may be derived partially or entirely from syngas. For example, the optional source of acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, acetic acid may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The optional source of acetic acid fed to the hydrogenation reactor, in some embodiments, may also comprise other carboxylic acids and anhydrides, as well as aldehydes and/or ketones, such as acetaldehyde and acetone. In addition, the optional source of acetic acid may comprise methyl acetate and ethyl acetate.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

D. Hydrogenation of Oxygenates

The oxygenates, including the optional source of acetic acid, may be vaporized at the reaction temperature, following which the vaporized components may be fed along with hydrogen in an undiluted state or diluted state with a relatively inert carrier gas, such as nitrogen, argon, helium, carbon dioxide and the like. For reactions run in the vapor phase, the temperature preferably is controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

In general, the hydrogenation reaction consumes at least two moles of hydrogen per mole of the oxygenates, including acetic acid and/or acetaldehyde. The molar ratio of hydrogen to acetic acid, for example, in the feed stream may vary from 100:1 to 1:100, e.g., from 50:1 to 1:50, from 20:1 to 1:2, or from 18:1 to 8:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of oxygenates, including acetic acid, to form ethanol is preferably conducted in the presence of a hydrogenation catalyst in the reactor. Suitable hydrogenation catalysts include catalysts comprising a first metal, oxides thereof or carbides thereof, and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal, oxides thereof, or carbides thereof selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In some embodiments, the first metal may comprise molybdenum carbide. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, rhodium, osmium, iridium, titanium, zinc, potassium, silver, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 25 wt. %, e.g., from 0.1 to 10 wt. %, from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, silver, and rhenium. More preferably, the third metal is selected from cobalt, palladium, and ruthenium. When present, the total weight of the third metal preferably is from 0.05 to 20 wt. %, e.g., from 0.1 to 10 wt. %, or from 0.1 to 5 wt. %.

In another embodiment, the catalyst may comprise two active metals or three active metals. The first metal, oxides thereof or carbides thereof may be selected from the group consisting of cobalt, rhodium, rhenium, ruthenium, platinum, palladium, osmium, iridium and gold. The second metal or oxides thereof may be selected from the group consisting of copper, iron, tin, cobalt, nickel, zinc, and molybdenum. The third metal or oxides thereof, if present, may be selected from the group consisting of copper, molybdenum, tin, chromium, iron, cobalt, vanadium, palladium, platinum, lanthanum, cerium, manganese, ruthenium, rhenium, gold, and nickel. Preferably, the third metal is different than the first metal and the second metal. In addition, the first metal and the second metal may be different, and the third metal and the second metal may be different.

The metal loadings of the first, second, and optionally third metals are as follows. The first active metal may be present in the catalyst in an amount from 0.05 to 20 wt. %, e.g. from 0.1 to 10 wt. %, or from 0.5 to 5 wt. %. The second active metal may be present in an amount from 0.05 to 20 wt. %, e.g., from 0.1 to 10 wt. %, or from 0.5 to 7.5 wt. %. The third metal, when present, may be present in the catalyst in an amount from 0.05 to 20 wt. %, e.g. from 0.1 to 10 wt. %, or from 0.1 to 5 wt. %. The active metals may be alloyed with one another or may comprise a non-alloyed metal solution, a metal mixture or be present as one or more metal oxides. For purposes of the present specification, unless otherwise indicated, weight percent is based on the total weight the catalyst including metal and support.

Bimetallic catalysts for some exemplary catalyst compositions include platinum/tin, platinum/ruthenium, platinum/rhenium, platinum/cobalt, platinum/nickel, palladium/ruthenium, palladium/rhenium, palladium/cobalt, palladium/copper, palladium/nickel, ruthenium/cobalt, gold/palladium, ruthenium/rhenium, ruthenium/iron, rhodium/iron, rhodium/cobalt, rhodium/nickel, cobalt/tin, rhodium/tin, molybdenum carbide/copper, and molybdenum carbide/palladium. More preferred bimetallic catalysts include platinum/tin, platinum/cobalt, platinum/nickel, palladium/cobalt, palladium/copper, palladium/nickel, ruthenium/cobalt, ruthenium/iron, rhodium/iron, rhodium/cobalt, rhodium/nickel, cobalt/tin, and rhodium/tin.

In some embodiments, the catalyst may be a ternary catalyst that comprises three active metals on a support. Exemplary tertiary catalysts may include palladium/tin/rhenium, palladium/cobalt/rhenium, palladium/nickel/rhenium, palladium/cobalt/tin, platinum/tin/palladium, platinum/tin/rhodium, platinum/tin/gold, platinum/tin/iridium, platinum/cobalt/tin, platinum/tin/chromium, platinum/tin/copper, platinum/tin/zinc, platinum/tin/nickel, rhodium/nickel/tin, rhodium/cobalt/tin, rhodium/iron/tin, palladium/rhenium/silver, palladium/gold/rhenium. More preferably, a ternary catalyst comprises three active metals may include palladium/cobalt/tin, platinum/tin/palladium, platinum/cobalt/tin, platinum/tin/chromium, platinum/tin/copper, platinum/tin/nickel, rhodium/nickel/tin, rhodium/cobalt/tin and rhodium/iron/tin.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). The calcium metasilicate may be crystalline or amorphous.

A preferred silica support material is SS61138 High Surface Area (HSA) Silica Catalyst Carrier from Saint-Gobain N or Pro. The Saint-Gobain N or Pro SS61138 silica exhibits the following properties: contains approximately 95 wt. % high surface area silica; surface area of 250 $m^2/g$; median pore diameter of 12 nm; average pore volume of 1.0 $cm^3/g$ as measured by mercury intrusion porosimetry and a packing density of 0.352 $g/cm^3$ (22 $lb/ft^3$).

A preferred silica/alumina support material is KA-160 silica spheres from Sud Chemie having a nominal diameter of 5 mm, a density of 0.562 g/ml, an absorptivity of 0.583 g $H_2O$/g support, a surface area of 160 to 175 $m^2/g$, and a pore volume of 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of oxygenates, including acetic acid, may achieve favorable conversion and favorable selectivity and productivity to ethanol in the reactor. For the purposes of the present invention, the term "conversion" refers to the net change of the flow of one of the oxygenates, such as acetic acid or acetaldehyde, into the reactor as compared to the flow of that oxygenate out of the reactor. Conversion may be expressed as a percentage based on the oxygenates in the feed. The conversion of acetic acid may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from one of the oxygenates has an independent selectivity and that selectivity is independent from conversion. For example, if 60 mole % of the converted acetic acid is converted to ethanol, we refer to the ethanol selectivity as 60%. The total selectivity refers to the combined selectivity for all the components in the oxygenate stream. Preferably, the catalyst has a total selectivity to ethanol is at least 60%, e.g., at least 70%, or at least 80%. Preferably, in the reactor, the total selectivity to ethanol is at least 80%, e.g., at least 85% or at least 88%. Preferred embodiments of the hydrogenation process also have low selectivity to gaseous byproducts, such as methane and carbon dioxide. The selectivity to these gaseous byproducts preferably is less than 4%, e.g., less than 2% or less than 1%.

Selectivity to ethane may vary with the amount of ethylene fed to the hydrogenation reactor. Although ethane may be produced in the absence of ethylene, higher amounts of ethane are formed in the hydrogenation reactor with increased concentrations of ethylene. In other embodiments, ethane selectivity may vary with the type of catalyst. In particular, some catalysts may favor formation of ethane, such as the palladium/rhenium and ruthenium/rhenium catalysts described in U.S. Pat. No. 5,149,680, the entire contents and disclosure of which is hereby incorporated by reference. The ethane selectivity reported in the '680 patent ranges from 2 to 14.19 wt. % for the palladium/rhenium and ruthenium/rhenium catalyst. When ethane is produced, the ethane may be concentrated and fed to the oxidation reactor and converted to ethylene or one or more oxygenates. In some embodiments, when ethylene is fed to the hydrogenation reaction, the selectivity to ethane may be increased under the hydrogenation conditions. The formed ethane may be returned to the oxidation reactor.

The term "productivity," as used herein, refers to the grams of a specified product, e.g., ethanol, formed during the hydrogenation based on the kilograms of the hydrogenation catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the reactor, before any subsequent processing, such as purification and separation, will typically comprise unreacted acetic acid, ethanol and water. The unreacted acid may be separated and returned to the hydrogenation reactor. The water may be separated and reacted with ethylene under hydration conditions to form ethanol. In some embodiments, the crude ethanol product may also comprise ethane, which may be separated and returned to the oxidation reactor.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, the process comprising the steps of:
    (a) contacting acetic acid and hydrogen in a first reactor under conditions effective to form a first reactor product comprising ethanol and from 0.5 to 10 mol % ethane;
    (b) separating the ethanol and ethane using liquid-vapor separation to form an ethanol stream and an ethane stream;
    (c) passing at least a portion of the ethane stream and oxygen to a second reactor to form a second reactor product comprising oxygenates; and
    (d) introducing at least a portion of the second reactor product into the first reactor.

2. The process of claim 1, wherein the second reactor product further comprises ethylene.

3. The process of claim 1, wherein when the second reactor product comprises more than 50 wt. % ethylene, step (c) further comprises:
    (i) separating the second reactor product to form an oxygenates stream and an ethylene stream; and
    (ii) feeding the oxygenates stream to the first reactor.

4. The process of claim 1, wherein step (c) further comprises:
    (i) separating the second reactor product to form an oxygenates stream and an ethylene stream; and
    (ii) feeding the oxygenates stream to the first reactor.

5. The process of claim 4, further comprising the steps of:
    (e) contacting the ethylene stream with water in a third reactor to form ethanol;
    (f) separating the ethanol and unreacted ethylene; and
    (g) combining the unreacted ethylene with the ethane from step (c).

6. The process of claim 1, wherein the second reactor product comprises more acetic acid than ethylene, on a weight basis.

7. The process of claim 1, wherein the oxygenates comprise acetaldehyde and/or acetic acid.

8. The process of claim 1, wherein the oxygenates comprise at least 80 wt. % acetic acid.

9. The process of claim 1, wherein the step (a) is conducted in the presence of a catalyst that comprises a first metal, oxides thereof, or carbides thereof selected from the group consisting of cobalt, rhodium, rhenium, ruthenium, platinum, palladium, osmium, iridium, molybdenum and gold, a second metal or oxides thereof selected from the group consisting of copper, iron, tin, cobalt, nickel, zinc, silver and molybdenum, and an optional third metal or oxides thereof selected from the group consisting of copper, molybdenum, tin, chromium, iron, cobalt, vanadium, palladium, platinum, lanthanum, cerium, manganese, ruthenium, rhenium, gold, and nickel, wherein the second metal is different than the first metal and the optional third metal.

10. The process of claim 1, wherein the step (c) is conducted in the presence of a catalyst comprising Mo, Pd, Re, and at least one other metal.

11. The process of claim 1, wherein the ethanol stream is substantially free of ethane.

12. The process of claim 1, wherein the ethane stream is substantially free of ethanol.

13. The process of claim 1, wherein the ethane stream comprises at least 90 vol. % ethane.

14. A process for producing ethanol, the process comprising the steps of:
 (a) providing a crude stream comprising ethanol and from 0.5 to 10 mol % ethane;
 (b) separating the ethanol and ethane using liquid-vapor separation to form an ethanol stream and an ethane stream;
 (c) passing at least a portion of the ethane and oxygen to a second reactor to form a second reactor product comprising oxygenates; and
 (d) introducing at least a portion of the second reactor product into a first reactor.

15. The process of claim 14, wherein the second reactor product further comprises ethylene.

16. A process for producing ethanol, the process comprising the steps of:
 (a) contacting a feedstream comprising ethylene and at least one of acetic acid or ethyl acetate with hydrogen in a first reactor, under conditions effective to form a first reactor product comprising ethanol and from 0.5 to 10 mol % ethane;
 (b) separating the ethanol and ethane using liquid-vapor separation to form an ethanol stream and an ethane stream;
 (c) passing at least a portion of the ethane stream and oxygen to a second reactor to form a second reactor product comprising oxygenates, ethylene, or mixtures thereof; and
 (d) introducing at least a portion of the second reactor product into the first reactor.

17. The process of claim 16, wherein the first reactor further comprises a polymerization inhibitor.

18. The process of claim 16, wherein the feedstream comprises ethylene and ethyl acetate.

* * * * *